(12) United States Patent
Katayose et al.

(10) Patent No.: US 9,403,036 B2
(45) Date of Patent: Aug. 2, 2016

(54) PARTICLE BEAM TREATMENT DEVICE AND OPERATION METHOD THEREFOR

(71) Applicant: Mitsubishi Electric Corporation, Chiyoda-ku, Tokyo (JP)

(72) Inventors: Tadashi Katayose, Tokyo (JP); Kengo Sugahara, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/652,992

(22) PCT Filed: Apr. 23, 2013

(86) PCT No.: PCT/JP2013/061920
§ 371 (c)(1),
(2) Date: Jun. 17, 2015

(87) PCT Pub. No.: WO2014/174592
PCT Pub. Date: Oct. 30, 2014

(65) Prior Publication Data
US 2016/0101297 A1    Apr. 14, 2016

(51) Int. Cl.
*A61N 5/10* (2006.01)
*G21K 1/093* (2006.01)

(52) U.S. Cl.
CPC ............ *A61N 5/1048* (2013.01); *A61N 5/1043* (2013.01); *A61N 2005/1074* (2013.01); *A61N 2005/1087* (2013.01)

(58) Field of Classification Search
CPC . A61N 5/1043; A61N 5/1048; A61N 5/1077; H05H 13/04
USPC ............ 250/492.3, 491.1, 493.1, 505.1, 398, 250/396 R; 600/1
See application file for complete search history.

(56) References Cited

U.S. PATENT DOCUMENTS 7,301,162 B2 * 11/2007 Matsuda .............. A61N 5/1043
250/491.1
8,421,031 B2 * 4/2013 Honda ................. A61N 5/1043
250/396 R
(Continued)

FOREIGN PATENT DOCUMENTS

JP    03-236862 A    10/1991
JP    8-298200 A    11/1996
(Continued)

OTHER PUBLICATIONS

International Search Report (PCT/ISA/210) mailed on May 28, 2013, by the Japanese Patent Office as the International Searching Authority for International Application No. PCT/JP2013/061920.

*Primary Examiner* — David A Vanore
(74) *Attorney, Agent, or Firm* — Buchanan Ingersoll & Rooney PC (57) ABSTRACT

When an energy of a particle beam to be emitted from an accelerator is set for every slice group including two or more adjacent slices and an attenuation amount is set for each slice in the slice group, the energy to be emitted from the accelerator is set, for every slice group, higher than an energy corresponding to the slice at a deepest location in that slice group so that a transmissive plate has a predetermined thickness for the slice at the deepest location; and, with respect to a thickness of the transmissive plate to be set for every slice group, the thickness set for the slice group at a deep location is larger than or equal to the thickness set for the slice group at a shallow location, and the thickness set for the slice group at a deepest location is thicker than the thickness set for the slice group at a shallowest location.

5 Claims, 6 Drawing Sheets

(56) References Cited

U.S. PATENT DOCUMENTS

| | | | |
|---|---|---|---|
| 9,067,066 B2 * | 6/2015 | Yamada | A61N 5/1048 |
| 2006/0102856 A1 * | 5/2006 | Matsuda | A61N 5/1043 250/492.22 |
| 2007/0164227 A1 | 7/2007 | Yoshida | |
| 2009/0032721 A1 | 2/2009 | Yoshida | |
| 2012/0228521 A1 * | 9/2012 | Honda | A61N 5/1043 250/492.3 |
| 2014/0323793 A1 * | 10/2014 | Yamada | A61N 5/1048 600/1 |
| 2016/0101297 A1 * | 4/2016 | Katayose | A61N 5/1043 600/1 |

FOREIGN PATENT DOCUMENTS

| | | |
|---|---|---|
| JP | 2006-034582 A | 2/2006 |
| JP | 2007-132902 A | 5/2007 |
| JP | 2007-185423 A | 7/2007 |
| JP | 2008-161716 A | 7/2008 |
| JP | 2010-238463 A | 10/2010 |

* cited by examiner

PARTICLE BEAM TREATMENT DEVICE AND OPERATION METHOD THEREFOR

TECHNICAL FIELD

The present invention relates, in particular, among particle beam treatment devices for performing a therapy by radiating a particle beam to a diseased site such as a tumor, to a particle beam treatment device for performing three-dimensional radiation and an operation method therefor.

BACKGROUND ART

In particle beam treatment devices, a particle beam (particle ray) emitted after being accelerated by a circular accelerator up to a given energy, is transported through a transport pathway to a particle beam irradiation apparatus placed in an irradiation room. In the particle beam irradiation apparatus, the supplied particle beam is radiated after being formed into a shape matched to an irradiation target. In recent years, for reducing an unwanted dose to normal tissues and for effective utilization of radial rays, attention has been paid to three-dimensional radiation. In the three-dimensional radiation, not only the shape in x-y direction (cross-section perpendicular to a beam traveling direction) is formed by scanning electromagnets, but also the shape in z-direction (the beam traveling direction) is formed by changing the energy.

Here, the following two ways are conceivable how to change the energy; one of which is to change a destination energy due to acceleration by a synchrotron (circular accelerator), and the other way is to cause deceleration by use of a variable range shifter capable of changing its attenuation amount by adjustment of the water-equivalent thickness of its transmissive plate. In order to achieve the three-dimensional radiation, a number of energy stages with one hundred levels, for example, are required. The pitches of these one hundred stages are determined to be the same pitch as a water-equivalent thickness (depth of Bragg peak in water). If these stages are to be achieved solely by changing the acceleration energy of the synchrotron, this results in performing hundred times of emission-adjustments of the synchrotron and adjustments of the transport system, and thus, there is a problem of spending a lot of time. Meanwhile, according to the variable range shifter, the more the thickness increases, the larger the scattering and/or the beam loss becomes, so that it is not desired that the required number (one hundred levels) of energy stages be all achieved solely by the variable range shifter.

In this respect, it is conceivable, for example, that half of the required number of stages (50 stages) are provided by the synchrotron as emission energies, while, with respect to respective intermediate levels therein, they are adjusted by changing the attenuation amount at the variable range shifter. At that time, in order to converge the spread particle beam due to scattering at the time of passing through the variable range shifter, it is conceivable to apply a technology of a particle beam irradiation apparatus in which a four-pole electromagnet is placed (see, for example, Patent Document 1).

CITATION LIST

Patent Document

Patent Document 1: Japanese Patent Application Laid-open No. 2007-185423 (Paragraphs 0008 to 0016, FIG. 1)
Patent Document 2: Japanese Patent Application Laid-open No. H03-236862 (Page 2, upper-right column to lower-left column, FIG. 1 to FIG. 3)
Patent Document 3: Japanese Patent Application Laid-open No. H08-298200 (Paragraphs 0010 to 0019, FIG. 1 to FIG. 5)

SUMMARY OF THE INVENTION

Problems to be Solved by the Invention

However, according to such a configuration, when the energy is changed successively, repetitive increase-decrease occurs in degree of scattering because of increase-decrease in the water-equivalent thickness of the variable range shifter. Thus, it was unable to perform such a control to monotonously decrease (or increase) the strength of the four-pole electromagnet as shown, for example in Patent Document 2 or Patent Document 3, for suppressing an influence of hysteresis of the magnetic member. Accordingly, the state of the particle beam supplied to the scanning electromagnets is unstable, so that it was difficult to perform accurate radiation.

The present invention has been made to solve the problem as described above, and an object thereof is to realize a particle beam therapy in which the state of the particle beam becomes stable, so that three-dimensional radiation can be made accurately.

Means for Solving the Problems

A particle beam treatment device of the invention is a particle beam treatment device in which, when an irradiation target is partitioned along a depth direction thereof into a plurality of slices and a particle beam formed for each of the slices is radiated thereto in a depth order, an energy of the particle beam to be emitted from an accelerator is set for every slice group including two or more adjacent ones of the slices, and an attenuation amount is set for each slice in said slice group. The particle beam treatment device is characterized by comprising: a variable range shifter that adjusts the attenuation amount by changing a thickness of its transmissive plate through which the particle beam is transmitted; an irradiation nozzle that has a scanning electromagnet and that makes forming of the particle beam adjusted in the attenuation amount, according to each of the slices; a four-pole electromagnet that is placed between the variable range shifter and the irradiation nozzle, and that operates so as to converge the particle beam having been spread by the transmissive plate; and a control unit that determines set values of the accelerator and the variable range shifter, and that controls an amount of magnetic excitation of the four-pole electromagnet according to the set values;

wherein, for said every slice group, the control unit sets higher the energy to be emitted from the accelerator than an energy corresponding to the slice at a deepest location in said slice group so that the transmissive plate has a predetermined thickness for the slice at the deepest location; and wherein, with respect to the thickness of the transmissive plate to be set for said every slice group, the thickness set for the slice group at a deep location is larger than or equal to the thickness set for the slice group at a shallow location, and the thickness set for the slice group at a deepest location is thicker than the thickness set for the slice group at a shallowest location.

An operation method of a particle beam treatment device of the invention is an operation method of a particle beam treatment device, which is characterized by comprising: when an irradiation target is partitioned along a depth direction thereof into a plurality of slices and a particle beam formed by an irradiation nozzle for each of the slices is radiated thereto in a depth order, setting an energy of the particle beam to be emitted from an accelerator for every slice group including two or more adjacent ones of the slices; setting an attenuation amount for each slice in said slice group by a variable range shifter; and converging the particle beam incident to the irradiation nozzle, by a four-pole electromagnet placed between the variable range shifter and the irradiation nozzle;

wherein, for said every slice group, a set value of the energy of the accelerator is set higher than an energy corresponding to the slice at a deepest location in said slice group so that the variable range shifter has a predetermined attenuation amount for the slice at the deepest location;

wherein, with respect to the attenuation amount to be set for said every slice group, the amount set for the slice group at a deep location is larger than or equal to the amount set for the slice group at a shallow location, and the amount set for the slice group at a deepest location is larger than the amount set for the slice group at a shallowest location; and wherein an amount of magnetic excitation of the four-pole electromagnet is controlled according to the set value of the energy of the accelerator and the attenuation amount by the variable range shifter.

Effect of the Invention

According to the particle beam treatment device or the operation method of the particle beam treatment device of the invention, when the energy is changed, the spread particle beam can be converged by monotonously changing the strength of the four-pole electromagnet, so that the state of the particle beam becomes stable and thus it is possible to perform a particle beam therapy in which three-dimensional radiation can be made accurately.

MODES FOR CARRYING OUT THE INVENTION

Embodiment 1

Figure 1:
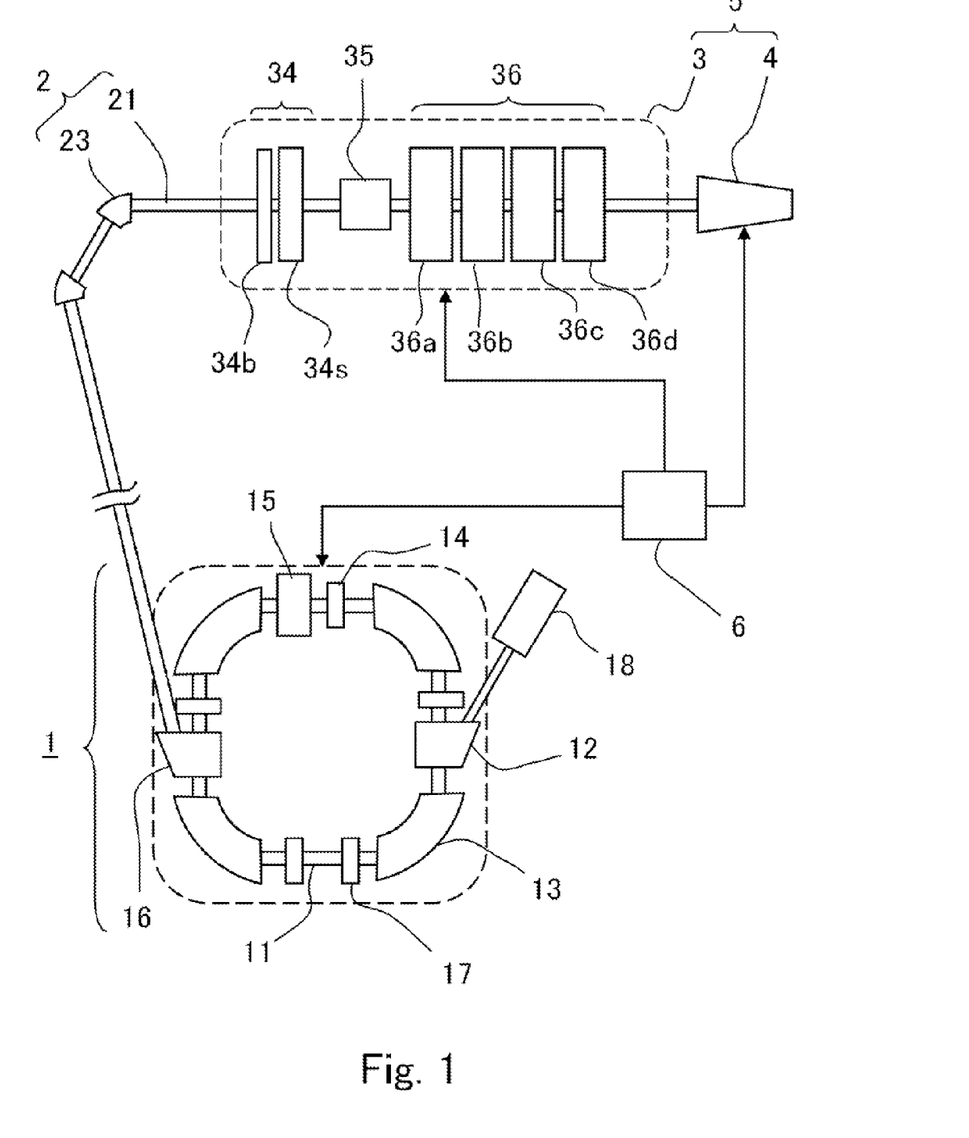
FIG. 1 is an apparatus arrangement diagram for illustrating a configuration of a particle beam treatment device according to Embodiment 1 of the invention.
Figure 2:
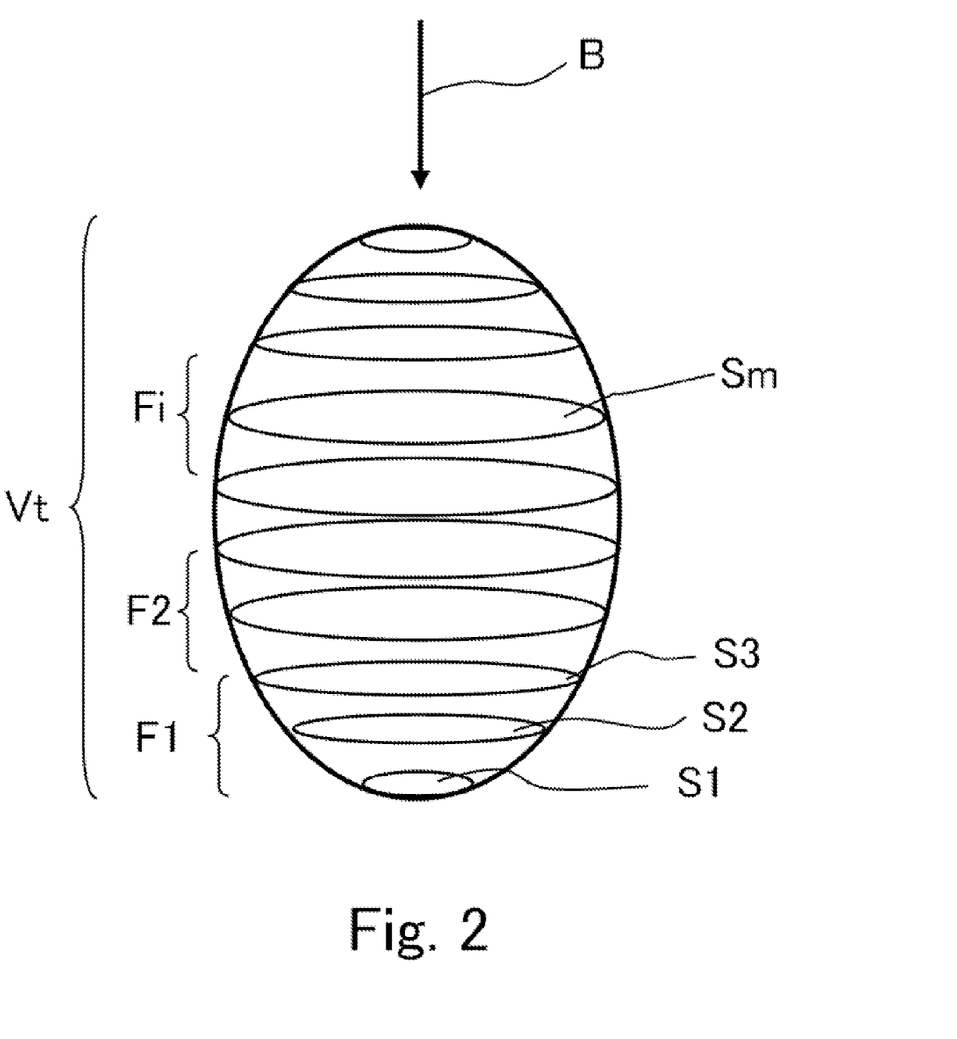
FIG. 2 is a schematic diagram showing an irradiation region at the time of performing three-dimensional radiation using the particle beam treatment device according to Embodiment 1 of the invention.
Figure 3:
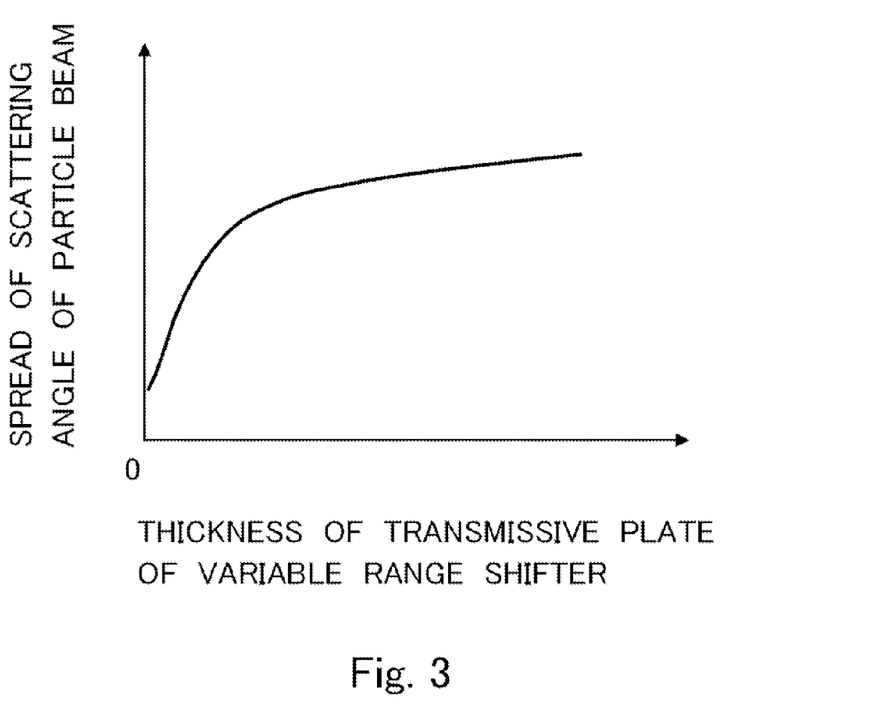
FIG. 3 is a graph showing a relationship between a thickness of a transmissive plate of a variable range shifter and a spread of scattering angle of a particle beam.
Figure 4:
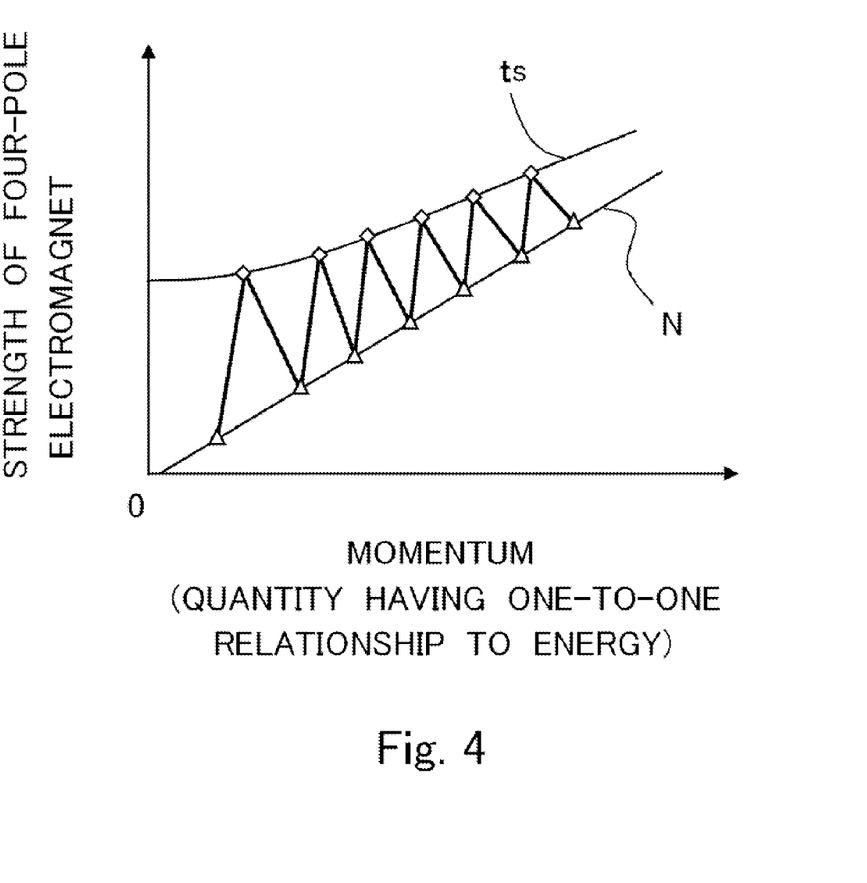
FIG. 4 is a graph for illustrating a required strength of a four-pole electromagnet at the time of adjusting energy, in a conventional particle beam treatment device.
Figure 5:
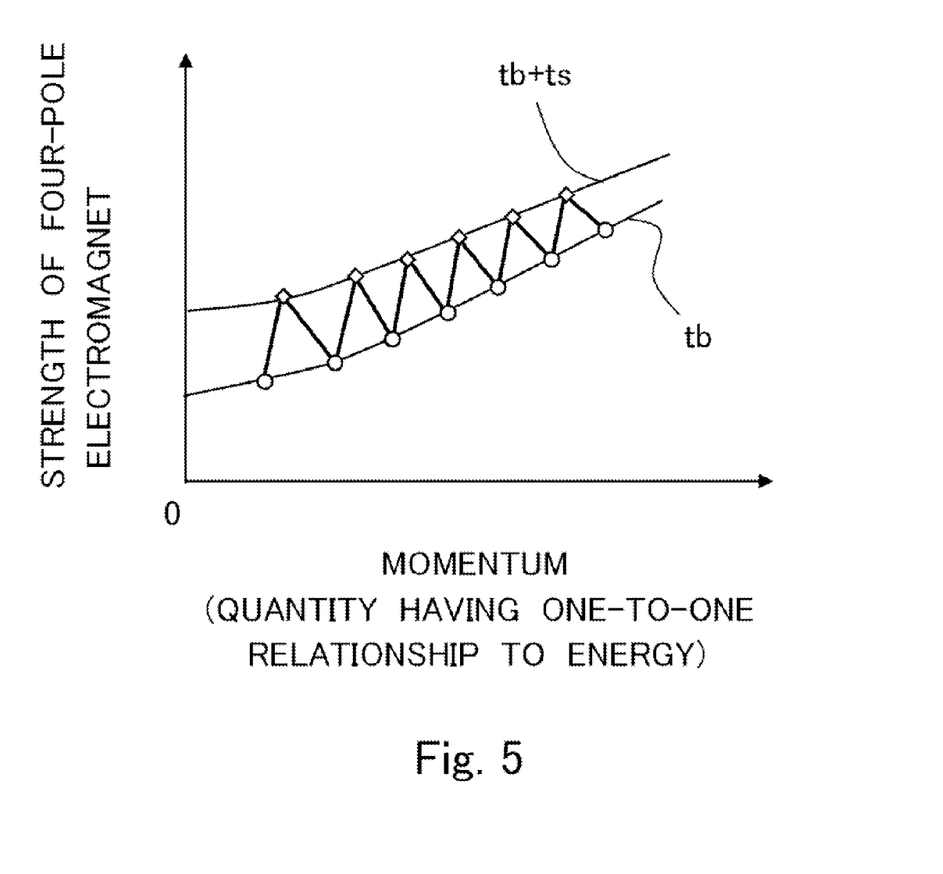
FIG. 5 is a graph for illustrating a required strength of a four-pole electromagnet at the time of adjusting energy, in another conventional particle beam treatment device.
Figure 6:
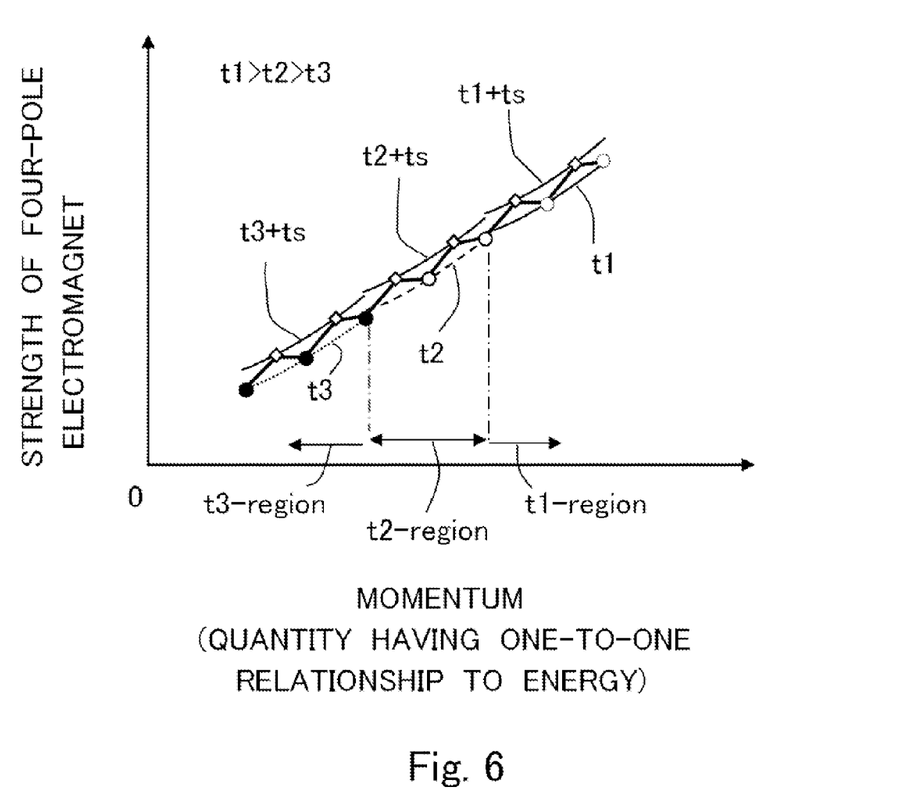
FIG. 6 is a graph for illustrating a required strength of a four-pole electromagnet at the time of adjusting energy, in the particle beam treatment device and an operation method of a particle beam treatment device according to Embodiment 1 of the invention.

Hereinafter, description will be made about a particle beam treatment device and an operation method of a particle beam treatment device, according to Embodiment 1 of the invention. FIG. 1 is a schematic diagram of an apparatus arrangement for illustrating a configuration of the particle beam treatment device according to Embodiment 1 of the invention, and FIG. 2 is a schematic diagram showing an irradiation region at the time of performing three-dimensional radiation, that is set by being partitioned in a depth direction into slices each having a predetermined thickness. FIG. 3 is a graph showing a relationship between a thickness of a transmissive plate of a variable range shifter for changing the energy and a spread of scattering angle of a particle beam, and FIG. 4 and FIG. 5 are graphs each for illustrating a relationship between a momentum (a quantity having one-to-one relationship to energy) of a particle beam and a strength of a four-pole electromagnet at the time three-dimensional radiation is performed using a particle beam treatment device of a conventional configuration. Further, FIG. 6 is a graph for illustrating a relationship between a momentum of a particle beam and a strength of a four-pole electromagnet at the time three-dimensional radiation is performed using the particle beam treatment device or the operation method of a particle beam treatment device according to Embodiment 1 of the invention.

The particle beam treatment device and the operation method of the particle beam treatment device according to Embodiment 1 of the invention are characterized by a configuration for adjusting energy in three-dimensional radiation or a method of adjusting the energy. However, prior to the description of these configuration and method, a whole configuration of the particle beam treatment device will be described using FIG. 1.

In the figure, the particle beam treatment device includes, as a source of supplying a particle beam, a circular accelerator which is a synchrotron (hereinafter, referred to simply as accelerator 1); a particle beam irradiation apparatus 5 capable of performing three-dimensional radiation; and a transport system 2 that connects between the accelerator 1 and the particle beam irradiation apparatus 5 so as to transport the particle beam from the accelerator 1 to the particle beam irradiation apparatus 5. Note that the transport system 2 has transport pathways connected to a plurality of the other unshown particle beam irradiation apparatuses in addition to the particle beam irradiation apparatus 5. Here, the particle beam emitted from the accelerator 1 can be supplied to any requesting one of the particle beam irradiation apparatuses by switching the trajectory using switching electromagnets. Note that, with respect to the other unshown particle beam irradiation apparatuses, they are not necessarily limited to having a function of three-dimensional radiation. Next, description will be turned to the respective configurations.

The accelerator 1 includes a vacuum duct 11 that provides a trajectory channel for causing charged particles to go around therethrough; an injection device 12 for injecting the charged particles supplied from a pre-accelerator 18 into the vacuum duct 11; deflection electromagnets 13 for deflecting the trajectory of the charged particles so that the charged particles circulate along the round trajectory in the vacuum duct 11; a four-pole electromagnet 14 that causes the charged particles on the round trajectory to converge so as not to diverge; a high-frequency acceleration cavity 15 that applies to the circulating charged particles, a high frequency voltage synchronous with the particles to thereby accelerate them; an emission device 16 for taking out from the accelerator 1 the charged particles accelerated in the accelerator 1, as a particle beam having a predetermined energy, so as to emit it to the transport system 2; and a six-pole electromagnet 17 that excites resonance in the round trajectory for emitting the particle beam from the emission device 16. Here, the charged particles in the round trajectory are accelerated by a high frequency electric field up to approx. 60% to 80% of the light velocity while being bent by the magnets, and emitted to the transport system 2.

The transport system 2 is referred to as HEBT (High Energy Beam Transport) system, and includes a vacuum duct 21 that provides a transport channel of the particle beam; the unshown switching electromagnets that are switching devices for switching the trajectory of the particle beam; and deflection electromagnets 23 that deflect the particle beam by a predetermined angle.

The particle beam irradiation apparatus 5 serves to perform three-dimensional radiation in which the particle beam supplied from the transport system 2 is radiated to the diseased site after being formed into an irradiation field matched to the size and depth of the irradiation target. Note that, in the description hereinafter, the traveling direction of the particle beam is defined as z-direction and the directions that determine a plane perpendicular to the traveling direction are defined as x-direction and y-direction. In order to form the shape in the z-direction, the particle beam irradiation apparatus 5 includes a variable range shifter 34, a collimator 35 and a four-pole electromagnet 36, which function as an energy adjustment system 3 for adjusting the energy of the particle beam. Further, it includes a ridge filter for spreading the width of the Bragg peak according to the thickness of the slice, and an irradiation nozzle 4 having a scanning electromagnet that causes scanning in the x-direction and a scanning electromagnet that causes scanning in the y-direction, for forming (scanning) the two-dimensional shape in the x-y plane.

The variable range shifter 34 is a device for changing the energy of the particle beam. It has a function of advancing/retracting each transmissive plate adjusted to have a predetermined water-equivalent thickness (for example, in the figure, a base transmissive plate 34b having a water-equivalent thickness tb, and an energy-adjustment transmissive plate 34s having a water-equivalent thickness ts) into/from an incident region of the particle beam. Accordingly, the energy of the incident particle beam is adjusted by being attenuated to the extent of energy corresponding to the water-equivalent thickness. For example in the case of a polyethylene plate having a density of 0.94 to 0.96 g/cm$^3$, an intended water-equivalent thickness can be obtained when the plate is given with a thickness calculated by dividing the water-equivalent thickness by the density.

The collimator 35 is a metal block or the like in which a predetermined through-hole is formed, and serves to limit the spread in a planer direction (x-y plane) of the irradiation field, which corresponds to a slit in an optical apparatus. The ridge filter is formed, for example, of many cone-like objects or cross-sectionally triangle plates that are arranged in a plane, so that if the inside of the irradiation field is assumed to be divided into many small regions, there are portions of the beam passing through different thicknesses in each small region. This provides an SOBP (Spread-Out Bragg Peak) in which the Bragg Peak region is spread out. Namely, by means of the ridge filter, the irradiation region in the z-direction (thickness) is adjusted to be matched to the slice that is described later. However, there is a case where no ridge filter is used, although shown in this example is a case where adjustment is made by the ridge filter according to the thickness of the slice.

The four-pole electromagnet 36 comprises two N poles and two S poles which are alternately and circularly arranged when viewed from the traveling direction of the particle beam, and functions with respect to one direction in the x-y plane, as if it is a convex lens in an optical apparatus, and functions with respect to the direction perpendicular thereto, as if it is a concave lens. Thus, for example, when a plurality of four-pole electromagnet units 36a, 36b, 36c, 36d are arranged as their poles are shifted to each other in the traveling direction of the beam, the trajectory of the beam is converged in a specified region. Note that, in Embodiment 1, a case is shown where four number of four-pole electromagnet units 36a to 36d are arranged; however, this is not limitative, and the number may be increased or decreased appropriately according to the design condition.

Besides, there are provided with a control unit 6 for controlling the accelerator 1, the energy adjustment system 3 and the irradiation nozzle 4 in their cooperative manner, so that the three-dimensional radiation that is described later is executed.

Next, the three-dimensional radiation using the particle beam irradiation apparatus 5 with the above-described configuration will be described.

On this occasion, as shown in FIG. 2, an irradiation region Vt corresponding to the irradiation target is partitioned along the traveling direction of a particle beam B (z-direction: depth) into slices $S_1, S_2, S_3, \ldots S_m, \ldots$ (collectively, slice(s) S) each having a predetermined thickness. Further, in the energy adjustment system 3, the energy of the particle beam supplied from the accelerator 1 is adjusted so that the particle beam adjusted to have an energy corresponding to a range of each slice S is provided to the irradiation nozzle 4.

At this time, in particular in the case of providing a high quality therapy like three-dimensional radiation, it is important to reproduce a radiation specified in a treatment plan as faithful as possible. Thus, it is required for the energy adjustment system 3 to reduce, in each slice S, variation in width of the particle beam supplied to the irradiation nozzle 4 (evaluated by the standard deviation σ of the spread) and in its beam strength (evaluated by the current value indicative of the dose per hour). Specifically, with respect to the width of the particle beam, it is required that, when the standard deviation 1σ of the particle beam supplied at the time of irradiating a given slice $S_m$ is 5 mm, the standard deviation 1σ at the adjacent slice $S_{m+1}$ falls within about 6 mm. Further, with respect to the beam strength, when the current value at the time of irradiating a given slice $S_m$ is 2 nA and the current value at the adjacent slice $S_{m+1}$ falls within about 3 nA, this allows a highly accurate radiation.

However, it becomes difficult to cause a highly accurate radiation, for example, when, in the case where the standard deviation 1σ of the particle beam supplied at the time of irradiating a given slice $S_m$ is 5 mm, the standard deviation 1σ at the adjacent slice $S_{m+1}$ varies to 10 mm; or with respect to the beam strength, when the current value at the time of irradiating a given slice $S_m$ is 2 nA and the current value at the adjacent slice $S_{m+1}$ varies up to about 6 nA.

Here, when the three-dimensional radiation (layer-stacking conformal irradiation) is to be performed for the irradiation region Vt illustrated in FIG. 2, each slice S is designed to have the same pitch as a water-equivalent thickness, and irradiation is made successively from the deepest slice S1 to a shallower-side one in the traveling direction of the beam. Namely, in the three-dimensional radiation, radiation is performed while being shifted by each one slice S from a high energy to a low energy. Note that there is also a case where radiation is performed while being shifted by each one slice S from a low energy to a high energy.

At that time, as described in BACKGROUND ART, emission-energy stages whose number is n-th part of the required number of the stages, are provided by the accelerator 1. Further, with respect to the values corresponding to (n−1) number of intermediates in each stage, they are adjusted by inserting or releasing the transmissive plate of the variable range shifter 34. Namely, the energy of the particle beam to be emitted from the accelerator 1 is set for every slice group F including two or more adjacent slices S and an attenuation value(s) is set for each slice S in the slice group F. In this case, since the intermediate values in each stage are at the same pitch, it suffices to prepare (n−1) number of transmissive plates each corresponding to a water-equivalent thickness of n-th part of the energy in each stage, and to change the thickness of the variable range shifter 34 successively in such a manner that the number of the transmissive plates are decreased in each stage from (n−1) to zero.

Note that, for simplifying description, in the following description, such a case is described in which n=2 is given so that the emission-energy stages whose number is a half of the required number of the stages are provided by the accelerator 1, and a single value (intermediate value) is set intermediately in each stage (slice group F) by the variable range shifter 34. Namely, an emission energy of the accelerator 1 is set for every slice group F including two slices S, and with respect to the respective two slices S in the slice group F, they are dealt with by adjusting the thickness of the transmissive plate of the variable range shifter 34.

The spread of scattering angle of the particle beam when passed through a physical transmissive plate such as the variable range shifter 34 in that manner, becomes large as the thickness increases, as shown in FIG. 3. Thus, according to the adjustment method as described above, even though the energy is reduced successively and monotonously, switching between causing and not causing to pass through a transmissive plate is done for each emission energy (slice group F) of the accelerator 1, which results in repetitive variation in the scattering amount.

In general, in the optical design of HEBT without using a transmissive plate such as the variable range shifter 34, the magnetic field strength (magnetic excitation strength) standardized by a momentum one to one correspondence with the energy, is constant. Meanwhile, in the case of passing through a transmissive plate, the scattering becomes stronger as the energy becomes lower, so that the relationship between the momentum (energy) and the magnetic field strength becomes non-linear; however, such a phenomenon that the smaller the momentum becomes, the lower the strength of the four-pole electromagnet is allowed, remains the same. However, as shown in FIG. 4, a curve (ts) in the case of passing through a transmissive plate is shifted toward the higher side of the four-pole electromagnet in comparison with a curve (N) in the case of not passing through the transmissive plate.

Namely, even the momentum is constant, when the thickness of the transmissive plate through which the particle beam passes is made thicker, it is required to increase the magnetic field strength of the four-pole electromagnet 36. As a result, even though the energy is decreased successively and monotonously, the strength of the four-pole electromagnet 36 required for converging the scattered beam becomes stronger and weaker repeatedly. Specifically, when a switching is made from a condition in a given stage (slice group F) that disallows passing through a transmissive plate (in the figure, Δ-mark), to a condition in the next stage that allows passing through the transmissive plate (in the figure, ◊-mark), this results in increase of the strength of the four-pole electromagnet 36.

In this respect, it is also conceivable to introduce a technology for reducing variation in the scattering angle at the time of inserting the energy-adjustment transmissive plate 34s for adjustment to an intermediate value, by always inserting the base transmissive plate 34b with a thin water-equivalent thickness, as described for example in Patent Document 1 (Paragraph 0021, FIG. 3). In this case, as shown in FIG. 5, the difference (in the strength of the four-pole electromagnet 36) between a curve (tb) in the case of using the base transmissive plate 34b and a curve (tb+ts) in the case of adding the energy-adjustment transmissive plate 34s (corresponding to the same thickness (ts) in FIG. 4) for adjustment to an intermediate value, becomes smaller than the difference in FIG. 4.

In this manner, when the difference in the required strength is made smaller using the base transmissive plate 34b, it is able to adjust not to increase the strength of the four-pole electromagnet 36 in a part of the energy region at the time the water-equivalent thickness of the transmissive plate of the variable range shifter 34 is increased (in the figure, at the transition from σ to ◊ in a momentum-decreasing direction). However, in all of the energy ranges for forming the SOBP for every patient, it was difficult to adjust the energy without increasing the strength of the four-pole electromagnet 36.

Thus, in the particle beam treatment device according to Embodiment 1, the thickness of the base transmissive plate 34b used for the slice group F with a small energy-set value (at a shallow position) is thinner than that of the base transmissive plate 34b used for the slice group F with a large energy-set value (at a deep position). Specific examples of energy adjustment method in Conventional Example 1 corresponding to FIG. 4 described above, Conventional Example 2 corresponding to FIG. 5, and Example of the particle beam treatment device or the operation method of the particle beam treatment device according to Embodiment 1, will be shown in Table 1.

TABLE 1

Specific Examples of Energy Setting Method

| Slice | | | S1 | S2 | ... | Sm | Sm + 1 | ... | Sn | Sn + 1 | ... |
|---|---|---|---|---|---|---|---|---|---|---|---|
| Slice Group | | | F1 | | ... | Fi | | ... | Fj | | ... |
| Corresponding Energy | | | E1 | E2 | ... | Em | Em + 1 | ... | En | En + 1 | ... |
| Adjustment Method | Conventional Example 1 | A | E1 | | ... | Ei | | ... | Ej + Eb | | ... |
| | | RS | — | ts | ... | — | ts | ... | — | ts | ... |
| | Conventional Example 2 | A | E1 + Eb | | ... | Ei + Eb | | ... | Ej + Eb | | ... |
| | | RS | tb | tb + ts | ... | tb | tb + ts | ... | tb | tb + ts | ... |
| | Example | region | t1-region | | ... | t2-region | | ... | t3-region | | |
| | | A | E1 + Et1 | | ... | Ei + Et2 | | ... | Ej + Et3 | | ... |
| | | RS | t1 | t1+ts | ... | t2 | t2 + ts | ... | t3 | t3 + ts | ... |

A: acceleration energy,
RS: thickness of range shifter
Note
that, $2 < i < j$, $E_k = E1 - (k - 1) \cdot \Delta E$, and $t1 > t2 > t3$.

In Table 1, indicated at the uppermost column is the number of each slice S, at the next column is the number of each slice group F, and at the subsequent column is the energy-set value for each slice S. It is assumed that the energy successively decreases by $\Delta E$ through the course along $E_1, E_2, \ldots$, namely, the energy is changed from going toward the deep side to going toward the shallow side on a same pitch basis. Further, when the all energies are divided into three regions, among these set values, respectively represented by $E_1$ and $E_2$ are set values in a maximum energy range, by $E_1$ and $E_{i+1}$ are set values in an intermediate energy range, and by $E_j$ and $E_{j+1}$ are set values in a minimum energy range. As to the other set values, their description is skipped here.

For example in Conventional Example 1, for two energy-set values ($E_k$ and $E_{k+1}$) in a slice group F, a particle beam with a common energy ($E_k$) is emitted from the accelerator 1 ("A" column). Further, there is shown that the energy is adjusted to that corresponding to the energy-set value for each slice S in the slice group F, by inserting or releasing the energy-adjustment transmissive plate 34s with the water-equivalent thickness is corresponding to $\Delta E$ ("RS" column).

Besides, in Conventional Example 2, for two energy-set values ($E_k$ and $E_{k+1}$) in a slice group F, a particle beam with a common energy ($E_k + E_b$) that is set higher than the set value ($E_k$) so as to compensate its portion attenuated by the base transmissive plate 34b, is emitted from the accelerator 1 ("A" column). Further, the energy is adjusted to that corresponding to the energy-set value for each slice S in the slice group F, by inserting or releasing the energy-adjustment transmissive plate 34s with the water-equivalent thickness is corresponding to $\Delta E$ ("RS" column).

In contrast, in Example, an energy range (region) is divided into three ranges, and in the region of a maximum range (referred to as t1-region), the base transmissive plate 34b having a first water-equivalent thickness t1 is used; in the region of an intermediate range (referred to as t2-region), the base transmissive plate 34b having a second water-equivalent thickness t2 that is thinner than the first water-equivalent thickness is used; and in the region of a minimum range (referred to as t3-region), the base transmissive plate 34b having a third water-equivalent thickness t3 that is thinner than the second water-equivalent thickness.

Thus, for each two energy-set values ($E_k$ and $E_{k+1}$) in each slice group F, a particle beam whose common energy emitted from the accelerator 1 is ($E_k + E_{t1}$) for the t1 region, ($E_k + E_{t2}$) for the t2-region, or ($E_k + E_{t3}$) for the t3 region, instead of the set energy ($E_k$), is emitted ("A" column) so that the portion attenuated by the base transmissive plate 34b set for that range is compensated. Further, the energy is adjusted to that corresponding to the energy-set value for each slice S in the slice group F, by inserting or releasing the energy-adjustment transmissive plate 34s with the water-equivalent thickness ts corresponding to $\Delta E$ ("RS" column).

Namely, as shown in FIG. 6, the energy is adjusted based on a set of curves that is different for each region with respect to the thickness combination of the transmissive plate of the variable range shifter 34, such as, a curve (t1) and a curve (t1+ts) in the t1-region, a curve (t2) and a curve (t2+ts) in the t2-region, and a curve (t3) and a curve (t3+ts) in the t3-region. This makes it possible to adjust the strength of the four-pole electromagnet 36 so that it is not increased but monotonously decreased including also the case where the strength is unchanged, in all of the energy ranges for forming the SOBP for every patient.

As a result, it is possible to suppress the influence of the hysteresis to thereby accurately control the magnetic field strength at the four-pole electromagnet 36, so that the state of the particle beam becomes stable, thus making it possible to perform a particle beam therapy in which three-dimensional radiation can be made accurately.

Further, in the case of the configuration as described above, if the radiation is performed while being shifted by each one slice S from a low energy to a high energy, it becomes possible to adjust the strength of the four-pole electromagnet 36 so that it is not decreased but monotonously increased including also the case where the strength is unchanged. Accordingly, also in that case, it is possible to suppress the influence of the hysteresis to thereby accurately control the magnetic field strength at the four-pole electromagnet 36, so that the state of the particle beam becomes stable, thus making it possible to perform a particle beam therapy in which three-dimensional radiation can be made accurately.

Note that, in the above description, a case of dividing energies into three regions has been described; however, this is not limitative. The energies may be divided by an appropriate number of two or more so long as the magnetic field strength can be controlled to monotonously decrease. In addition, the number may be changed for each of the emission energies of the accelerator 1. Further, in the above description, a case has been described where the base transmissive plates 34b different in water-equivalent thickness are used separately for each region; however, this is not limitative. With respect to the adjustment of a water-equivalent thickness (attenuation amount) as the variable range shifter 34, it is also allowable to provide transmissive plates each adjusted to have the water-equivalent thickness to be intended; instead, the adjustment may be achieved by way of a so-called binary method in which the water-equivalent thickness to be intended is obtained by a combination of a plurality of transmissive plates having a twofold relationship in thickness between the respective transmissive plates.

Further, with the particle beam treatment device according to Embodiment 1, a configuration has been shown in which the energy adjustment system 3 is placed as a part of the particle beam irradiation apparatus 5 provided in each irradiation room; however, this is not limitative. For example, it may be placed in the transport system 2 at its portion common to the respective irradiation rooms.

Furthermore, with the particle beam treatment device according to Embodiment 1, a case has been described in which the irradiation nozzle 4 for forming an irradiation shape in a plane perpendicular to the traveling direction of the beam performs scanning irradiation for which an accuracy of the supplied beam is required; however, this is not limitative. For example, even in the case of such a wobbler method in which an irradiation field enlarged by a scanning electromagnet is formed into an irradiation shape by the use of a limiter having a physical transmissive shape, such as a multileaf collimator or the like, it is possible to cause irradiation with an accurate dose distribution because the accuracy of the beam supplied scanning electromagnets becomes higher.

As described above, in accordance with the particle beam treatment device according to Embodiment 1, when the irradiation target is partitioned along a depth direction thereof into a plurality of slices S and a particle ray (particle beam) formed for each of the slices S is radiated thereto in a depth order, the energy of the particle beam to be emitted from the accelerator 1 is set for every slice group F including two or more adjacent ones of the slices S, and the attenuation amount is set for each slice S in said slice group F. The particle beam treatment device is configured to includes: the variable range shifter 34 that adjusts the attenuation amount by changing the thickness of the transmissive plate through which the particle beam is transmitted; the irradiation nozzle 4 that has a scanning electromagnet and that makes forming of the particle beam adjusted in the attenuation amount, according to each of the slices S; the four-pole electromagnet 36 that is placed between the variable range shifter 34 and the irradiation nozzle 4, and that operates so as to converge the particle beam having been spread by the transmissive plate; and the control unit 6 that determines set values of the accelerator 1 and the variable range shifter 34, and that controls the amount of magnetic excitation of the four-pole electromagnet 36 according to the set values; wherein, for said every slice group F, the control unit 6 sets higher the energy to be emitted from the accelerator 1 than an energy corresponding to the slice S at a deepest location in said slice group F so that the transmissive plate has a predetermined thickness for the slice S at the deepest location; and wherein, with respect to the thickness of the transmissive plate to be set for said every slice group F, the thickness set for the slice group F at a deep location is larger than or equal to the thickness set for the slice group F at a shallow location, and the thickness set for the slice group F at a deepest location is thicker than the thickness set for the slice group F at a shallowest location. Thus, the spread particle beam can be converged by controlling the strength of the four-pole electromagnet 36 to monotonously decrease (or increase), so that the state of the particle beam becomes stable, thus making it possible to perform a particle beam therapy in which three-dimensional radiation can be made accurately.

In particular, since the irradiation nozzle 4 serves to perform the forming according to each slice S by use of a scanning method and thus requires, in particular, a stability of the beam incident to the irradiation nozzle 4, the effect of the invention emerges more significantly.

Further, since the collimator 35 for limiting passing of the particle beam spread out to a predetermined extent or more is placed between the variable range shifter 34 and the four-pole electromagnet 36, the spread particle beam can be converged more easily by controlling the strength of the four-pole electromagnet 36 to monotonously decrease (or increase).

Further, in accordance with the operation method of the particle beam treatment device according to Embodiment 1, when the irradiation target is partitioned along a depth direction thereof into a plurality of slices S and a particle beam formed by the irradiation nozzle 4 for each of the slices S is radiated thereto in a depth order, the energy of the particle beam to be emitted from the accelerator 1 is set for every slice group F including two or more adjacent ones of the slices S; the attenuation amount for each slice S in said slice group F, is set by the variable range shifter 34; and the particle beam incident to the irradiation nozzle 4 is converged by the four-pole electromagnet 36 placed between the variable range shifter 34 and the irradiation nozzle 4. The operation method of the particle beam treatment device is configured so that: for said every slice group F, the set value of the energy of the accelerator 1 is set higher than an energy corresponding to the slice S at a deepest location in said slice group F so that the variable range shifter 34 has a predetermined attenuation amount for the slice S at the deepest location; with respect to the attenuation amount to be set for said every slice group F, the amount set for the slice group F at a deep location is larger than or equal to the amount set for the slice group F at a shallow location, and the amount set for the slice group F at a deepest location is larger than the amount set for the slice group F at a shallowest location; and the amount of magnetic excitation of the four-pole electromagnet 36 is controlled according to the set value of the energy of the accelerator 1 and the attenuation amount by the variable range shifter 34. Thus, the spread particle beam can be converged by controlling the strength of the four-pole electromagnet 36 to monotonously decrease (or increase), so that the state of the particle beam becomes stable, thus making it possible to perform a particle beam therapy in which three-dimensional radiation can be made accurately.

DESCRIPTION OF REFERENCE NUMERALS AND SIGNS

1: accelerator, 2: transport system, 3: energy adjustment system, 4: irradiation nozzle, 5: particle beam irradiation apparatus, 34: variable range shifter, 34b: base transmissive plate, 34s: energy-adjustment transmissive plate, 35: collimator, 36: four-pole electromagnet, F: slice group, S: slice, Vt: irradiation region.

The invention claimed is:

1. A particle beam treatment device in which, when an irradiation target is partitioned along a depth direction thereof into a plurality of slices and a particle beam formed for each of the slices is radiated thereto in a depth order, an energy of the particle beam to be emitted from an accelerator is set for every slice group including two or more adjacent ones of the slices, and an attenuation amount is set for each slice in said slice group, said particle beam treatment device comprising:
a variable range shifter that adjusts the attenuation amount by changing a thickness of its transmissive plate through which the particle beam is transmitted;
an irradiation nozzle that has a scanning electromagnet and that makes forming of the particle beam adjusted in the attenuation amount, according to each of the slices;
a four-pole electromagnet that is placed between the variable range shifter and the irradiation nozzle, and that operates so as to converge the particle beam having been spread by the transmissive plate; and
a control unit that determines set values of the accelerator and the variable range shifter, and that controls an amount of magnetic excitation of the four-pole electromagnet according to the set values;
wherein, for said every slice group, the control unit sets higher the energy to be emitted from the accelerator than an energy corresponding to the slice at a deepest location in said slice group so that the transmissive plate has a predetermined thickness for the slice at the deepest location; and
wherein, with respect to the thickness of the transmissive plate to be set for said every slice group, the thickness set for the slice group at a deep location is larger than or equal to the thickness set for the slice group at a shallow location, and the thickness set for the slice group at a deepest location is thicker than the thickness set for the slice group at a shallowest location.

2. The particle beam treatment device of claim 1, wherein the irradiation nozzle makes said forming in accordance with the slice by a scanning method.

3. The particle beam treatment device of claim 1, wherein a collimator for limiting passing of the particle beam spread out to a predetermined extent or more, is placed between the variable range shifter and the four-pole electromagnet.

4. The particle beam treatment device of claim 2, wherein a collimator for limiting passing of the particle beam spread out to a predetermined extent or more, is placed between the variable range shifter and the four-pole electromagnet.

5. An operation method of a particle beam treatment device, comprising: when an irradiation target is partitioned along a depth direction thereof into a plurality of slices and a particle beam formed by an irradiation nozzle for each of the slices is radiated thereto in a depth order, setting an energy of the particle beam to be emitted from an accelerator for every slice group including two or more adjacent ones of the slices;

setting an attenuation amount for each slice in said slice group, by a variable range shifter; and converging the particle beam incident to the irradiation nozzle, by a four-pole electromagnet placed between the variable range shifter and the irradiation nozzle;

wherein, for said every slice group, a set value of the energy of the accelerator is set higher than an energy corresponding to the slice at a deepest location in said slice group so that the variable range shifter has a predetermined attenuation amount for the slice at the deepest location;

wherein, with respect to the attenuation amount to be set for said every slice group, the amount set for the slice group at a deep location is larger than or equal to the amount set for the slice group at a shallow location, and the amount set for the slice group at a deepest location is larger than the amount set for the slice group at a shallowest location; and wherein an amount of magnetic excitation of the four-pole electromagnet is controlled according to the set value of the energy of the accelerator and the attenuation amount by the variable range shifter.

\* \* \* \* \*